(12) United States Patent
Hirota

(10) Patent No.: US 8,778,965 B2
(45) Date of Patent: Jul. 15, 2014

(54) LOTION PREPARATION CONTAINING PYRIDONECARBOXYLIC ACID DERIVATIVE

(75) Inventor: Tsuyoshi Hirota, Kyoto (JP)

(73) Assignee: Maruho Co., Ltd., Osaka (JP)

(*) Notice: Subject to any disclaimer, the term of this patent is extended or adjusted under 35 U.S.C. 154(b) by 1545 days.

(21) Appl. No.: 11/989,850

(22) PCT Filed: Jul. 31, 2006

(86) PCT No.: PCT/JP2006/315129
§ 371 (c)(1),
(2), (4) Date: Jan. 31, 2008

(87) PCT Pub. No.: WO2007/015453
PCT Pub. Date: Feb. 8, 2007

(65) Prior Publication Data
US 2010/0099704 A1     Apr. 22, 2010

(30) Foreign Application Priority Data

Aug. 1, 2005  (JP) ................................ 2005-222825

(51) Int. Cl.
*A01N 43/42* (2006.01)
*A61K 31/47* (2006.01)
*C07D 215/00* (2006.01)

(52) U.S. Cl.
USPC ............................ 514/312; 514/314; 546/156

(58) Field of Classification Search
USPC .................................. 514/312, 314; 546/156
See application file for complete search history.

(56) References Cited

U.S. PATENT DOCUMENTS 4,976,953 A * 12/1990 Orr et al. .......................... 424/47
6,335,447 B1 * 1/2002 Hayashi et al. ............... 546/156

FOREIGN PATENT DOCUMENTS

| JP | 7-2670 | 1/1995 |
| JP | 07-330505 | 12/1995 |
| JP | 10-231248 | 9/1998 |
| JP | 2002-356426 | 12/2002 |
| WO | WO 03/063745 A1 | 8/2003 |
| WO | WO 2005/094788 A1 | 10/2005 |

OTHER PUBLICATIONS

Impurities: Residual Solvents (Maintenane) PDE for N-Methylpyrrolidone (NMP) Q3C(M), ICH Harmonised Tripartite Guideline, 2002, International Conference on Harmonisation of Technical Requirements for Registration of Pharmaceuticals for Human Use, pp. 2-4, Sep. 12, 2002, ICH Steering Committee.

* cited by examiner

Primary Examiner — Sarah Pihonak
(74) Attorney, Agent, or Firm — Kirschstein, et al.

(57) ABSTRACT

It is intended to provide a lotion preparation which exerts an excellent antibacterial effect, is excellent in the stability of active ingredient and does not contain an additive having a safety problem. The lotion preparation contains (a) 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof, (b) a lower alcohol, (c) a water-soluble polymer and (d) a polyhydric alcohol and the pH of the preparation is in the range of 9 to 12.

20 Claims, 2 Drawing Sheets

LOTION PREPARATION CONTAINING PYRIDONECARBOXYLIC ACID DERIVATIVE

TECHNICAL FIELD

The present invention relates to a lotion preparation containing a pyridonecarboxylic acid derivative or a pharmaceutically acceptable salt thereof which is useful as a medicine, in particular to a lotion preparation containing pyridonecarboxylic acid or a pharmaceutically acceptable salt thereof having an antimicrobial action as an active ingredient that is effective for treatment of, for example, dermal infectious diseases including acne and folliculitis.

BACKGROUND ART

Multiple factors are involved in onset of acne and folliculitis, but the most important factor is the growth of some Gram-positive anaerobic bacteria such as an *Propionibacterium acnes* and *Staphylococcus* in pilosebaceous ducts.

Conventionally, as the main treatment method of acne and folliculitis, an external antibacterial drug such as nadifloxacin has been frequently used for treatment of mild to moderate, while an oral antibacterial drug such as minocycline or roxithromycin has been frequently used for moderate to severe. However, such external antibacterial drugs were not sufficiently effective, and the oral drugs had severe problems of adverse effects during long-term administration and an increase in resistant bacteria.

Normally, the efficacy of an external therapy with an antibacterial drug is largely dependent not only on the antimicrobial activity of the active ingredient, but also on the thickness of the stratum corneum in the affected area and the penetration efficiency of the antibacterial drug into the corneum. Thus, it is important that an antimicrobial preparation is compatible with the skin and that it should contain an antibacterial drug that is completely dissolved uniformly and superior in stability, and also highly penetrable.

One reason for the difficulty of complete healing only with an external antibacterial drug is that it is difficult to deliver the active ingredient to the region under the stratum corneum or the hair follicle, where skin indigenous bacteria such as the *Propionibacterium acnes* and *Staphylococcus* generally proliferate.

As an example of a preparation that allows rapid penetration of the active ingredient deep into the skin, a skin external preparation containing a pyridonecarboxylic acid derivative, N-methylpyrrolidone, oleic acid, and propylene glycol (Patent Document 1) is proposed.

However, N-methylpyrrolidone is included in the Class 2 solvents, of which the blending amount should be restricted, in the guideline "Q3C Impurities: Residual Solvents" of medicines revised by the International Conference on Harmonization of Technical Requirements for Registration of Pharmaceuticals for Human Use (ICH) in October 2002, and thus, use of N-methylpyrrolidone is preferably avoided wherever possible (Nonpatent Document 1). Use of N-methylpyrrolidone should also be avoided from the viewpoint of safety.
Patent Document 1: Japanese Laid-open Patent Publication No. 2002-356426
Nonpatent Document 1: PDE for N-Methylpyrrolidone (NMP) Q3C (M), Residual Solvents, ICH Harmonised Tripartite Guideline

DISCLOSURE OF THE INVENTION

Problems to be Solved by the Invention

Accordingly, an object of the present invention is to provide a lotion preparation, aimed at treating acne and folliculitis, that (1) exhibits an excellent antimicrobial effect as the active ingredient antibacterial drug penetrates rapidly into the region below the stratum corneum, (2) is superior in the stability of the active ingredient, and (3) is free from an additive with a safety problem such as N-methylpyrrolidone, thereby providing a preparation excellent in safety and the antimicrobial effect.

Means for Solving the Problems

Through intensive studies under these circumstances, the inventors have found that it is possible to overcome the above problems with a lotion preparation containing a particular pyridonecarboxylic acid derivative, a lower alcohol, a water-soluble polymer and a polyhydric alcohol, and completed the present invention.

Accordingly, the present invention provides a lotion preparation containing
(a) 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof,
(b) a lower alcohol,
(c) a water-soluble polymer, and
(d) a polyhydric alcohol, and
having a pH of 9 to 12.

Effects of the Invention

Since the lotion preparation according to the present invention contains a pyridonecarboxylic acid derivative which is superior in antimicrobial activity as an active ingredient and is designed to make the active ingredient penetrate into the skin efficiently, the lotion preparation exhibits a superior therapeutic effect to various diseases including skin infectious diseases such as acne and folliculitis. It is also effective, safe, and hardly irritant to the application site.

BEST MODE OF CARRYING OUT THE INVENTION

Figure 1:
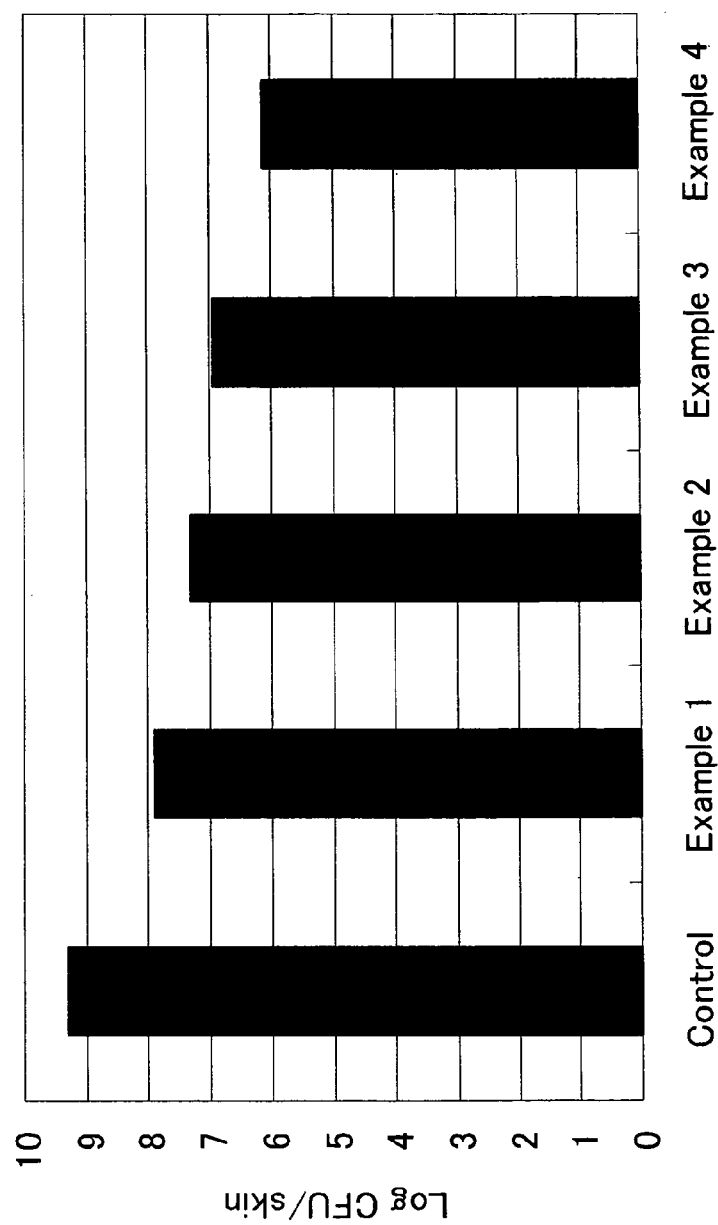
FIG. 1 is a graph showing the results of a pharmacological effectiveness test.

The pharmaceutically acceptable salts of 1-cyclopropyl-8-methyl-7-[5-methyl-6-(methylamino)-3-pyridyl]-4-oxo-1,4-dihydro-3-quinolinecarboxylic acid usable in the present invention (hereinafter, referred to as the pyridonecarboxylic acid derivative according to the invention) include commonly known salts of a basic group such as an amino group and salts of an acidic group such as a hydroxyl group or a carboxyl group.

Examples of the salts of the basic group include salts with a mineral acid such as hydrochloric acid, hydrobromic acid, or sulfuric acid; salts with an organic carboxylic acid such as tartaric acid, formic acid, fumaric acid, maleic acid, malic acid or citric acid; and salts with a sulfonic acid such as methanesulfonic acid, benzenesulfonic acid, p-toluenesulfonic acid, mesitylenesulfonic acid or naphthalenesulfonic acid.

Examples of the salts of the acidic group include salts with an alkali metal such as sodium or potassium; salts with an alkali-earth metal such as calcium or magnesium; an ammonium salt; and salts with a nitrogen-containing organic base such as an amino acid (such as lysine, arginine or ornithine), trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-◘-phenethylamine, 1-ephenamine or N,N'-dibenzylethylenediamine; and the like.

The content of the pyridonecarboxylic acid derivative according to the invention and/or the pharmaceutically acceptable salt thereof in the lotion preparation according to the present invention is not particularly limited as long as it is an amount capable of exhibiting a therapeutic effect, but it is normally 0.01 to 20 wt %, preferably 0.1 to 5 wt % in the lotion preparation.

The lower alcohol usable in the present invention is not particularly limited as long as it is a C1 to C3 alcohol, and examples thereof include methanol, ethanol, propanol, and isopropanol. Ethanol and isopropanol are preferable, and ethanol is particularly preferable. The blending amount is 1 to 20 wt %, preferably 5 to 10 wt % in the lotion preparation according to the present invention.

The polyhydric alcohol usable in the present invention is not particularly limited as long as it is an alcohol having two or more hydroxyl groups in a molecule and is used commonly in external preparations and cosmetics, and examples thereof include ethylene glycol, diethylene glycol, triethylene glycol, polyethylene glycol, propylene glycol, dipropylene glycol, hexylene glycol, 1,3-butylene glycol, glycerol, diglycerol, polyglycerol, sorbitol, xylitol, mannitol and the like. Preferably, it is 1,3-butylene glycol. These alcohols may be used alone or in combination of two or more, and the blending amount is 1 to 30 wt % in the lotion preparation according to the present invention.

The water-soluble polymer usable in the present invention is not particularly limited as long as it is commonly used in external preparations and cosmetics, and examples thereof include polyoxyethylene polymers such as polyethylene glycol 400, polyethylene glycol 4000, polyethylene glycol 20000, polyethylene glycol 4000000 and polyethylene glycol 600000; polyoxyethylene polyoxypropylene copolymers; acrylic polymers such as sodium polyacrylate, polyethyl acrylate and polyacrylamide; and cellulose derivatives such as methylcellulose, hydrophobized hydroxypropylmethylcellulose, hydroxyethylcellulose, and hydroxypropylcellulose. Cellulose derivatives are preferable, and hydroxyethylcellulose is more preferable. These compounds may be used alone or in combination of two or more, and the blending amount is 0.1 to 5 wt %, preferably 0.7 to 2 wt % in the lotion preparation according to the present invention.

The pH adjustor usable in the present invention is not particularly limited as long as it is a compound capable of adjusting the pH to 9 to 12 and having a buffering ability, and examples thereof include metal hydroxides such as sodium hydroxide, potassium hydroxide and lithium hydroxide; hydroxylated lower alkylamines such as monoethanolamine, monoisopropanolamine, diethanolamine, diisopropanolamine, triethanolamine, triisopropanolamine and 2-amino-2-methyl-1,3-propanediol; weak acid metal salts such as sodium bicarbonate, sodium citrate, sodium lactate, disodium hydrogenphosphate, and sodium tartrate; and the like, and preferable are metal hydroxides and weak acid metal salts, and more preferable are potassium hydroxide and sodium bicarbonate. These pH adjustors may be used alone or in combination of two or more, and the blending amount is 0.01 to 20 wt %, preferably 0.1 to 2 wt %, in the lotion preparation according to the present invention.

A stabilizer and the like may be further added within the scope of the object of the present invention. Examples of the stabilizers include ascorbic acid, sodium edetate, sodium thiosulfate, sodium sulfite, sodium pyrosulfite, sodium nitrite, sodium hydrogen sulfite, a photosensitizing dye 201, and the like. The lotion preparation according to the present invention exerts a storage effect without addition of a preservative, but a preservative may be added as needed.

The administration amount and the administration frequency of the lotion preparation according to the present invention are determined properly according to the age, body weight and symptom of the individual patient. Normally, a pharmaceutically effective amount is administered percutaneously all at once or as divided into several portions per day, and specifically, 30 to 2,000 mg per day of the lotion preparation may be administered percutaneously all at once or as divided into several portions.

The method of producing the liquid lotion preparation according to the present invention is not particularly limited. For example, a prescribed amount of the pyridonecarboxylic acid derivative according to the invention is dissolved in a prescribed amount of purified water previously adjusted to a suitable pH with an acid or an alkali (a principal drug phase). Separately, a gel base such as a water-soluble polymer is swollen and dissolved in purified water; and prescribed amounts of an additive dissolved in purified water and/or an aqueous base component such as lower alcohol or polyhydric alcohol are added thereto, to give a mixture solution (an additive phase). Subsequently, the principal drug phase and the additive phase are mixed with each other to give a desired lotion preparation. Alternatively, it is also possible to obtain a desired lotion preparation by mixing the principal drug phase and the additive phase, adding a suitable amount of an aqueous base component thereto, and finally adjusting the total amount of the lotion preparation by using the remaining aqueous base component.

Hereinafter, the present invention will be described more specifically with reference to Examples and Test Examples, but it should be understood that the present invention is not restricted by these Examples.

EXAMPLES

TABLE 1

| Composition (wt %) | Example 1 | Example 2 | Example 3 | Example 4 |
|---|---|---|---|---|
| Compound A | 0.25 | 0.5 | 1 | 2 |
| Hydroxyethylcellulose | 1.2 | 1.2 | 1.2 | 1.2 |
| 1,3-Butylene glycol | 15 | 15 | 15 | 15 |
| Ethanol | 5 | 5 | 5 | 5 |
| Potassium hydroxide | 0.265 | 0.31 | 0.4 | 0.58 |
| Sodium bicarbonate | 0.5 | 0.5 | 0.5 | 0.5 |
| Stabilizer | Quantum sufficiat | Quantum sufficiat | Quantum sufficiat | Quantum sufficiat |
| Purified water | Balance | Balance | Balance | Balance |
| pH | 10.9 | 10.9 | 10.9 | 10.9 |

TABLE 1-continued

| Composition (wt %) | | Example 1 | Example 2 | Example 3 | Example 4 |
|---|---|---|---|---|---|
| Appearance | Initial | Slightly yellow and clear | Pale yellow and clear | Pale yellow and clear | Yellow and clear |
| | 40° C./75% RH 13 weeks | Slightly yellow and clear | Pale yellow and clear | Pale yellow and clear | Yellow and clear |
| Stability | 40° C./75% RH 13 weeks | 99.9% | 100.2% | 99.9% | 99.5% |

Example 1

Preparation of Lotion Preparation

According to the composition ratio shown in Table 1, hydroxypropylcellulose was dissolved in a suitable amount of purified water, a 10% potassium hydroxide solution and 1-cyclopropyl-8-methyl-7-[5-methyl-6-(methylamino)-3-pyridyl]-4-oxo-1,4-dihydro-3-quinolinecarboxylic acid (referred to as a compound A in Examples) were added and dissolved therein in this order. In addition, 1,3-butylene glycol, ethanol and sodium bicarbonate were added and dissolved therein. Finally, the remaining amount of purified water was added to give a desired lotion preparation.

Examples 2 to 4

Preparation of Lotion Preparations

Desired lotion preparations were prepared in a similar manner to Example 1 according to the composition ratios shown in Table 1.

Test Example 1 pH Test

The pH of the lotion preparation in each Example was determined directly by using a pH meter (manufactured by Horiba, Ltd.).

Test Example 2

Stability Test

After each of the lotion preparations in Examples 1 to 4 was filled in a container and the appearance thereof was observed visually, the lotion preparation was stored under a condition of 40° C. and a relative humidity of 75% for 13 weeks. The appearance of the lotion preparation after storage was observed visually, and the content of the compound A was also determined.

In measuring the content of the compound A, a preparation in an amount corresponding to approximately 5 mg of the compound A was weighed, a diluted phosphoric acid solution and an internal standard solution were added thereto, and a part of the mixture thus obtained was used as the sample solution, in which the content of the compound A was measured by reversed-phase high-performance liquid column chromatography (detection wavelength: 265 nm, mobile phase; phosphate buffer solution (pH=2.0)/acetonitrile/water=5/4/12).

The content of the compound A in the sample solution is shown in Table 1, as a relative rate to the amount added during production of the preparation. As is obvious from Table 1, all lotion preparations were excellent in stability.

Test Example 3

Pharmacological Effectiveness Test

The pharmacological effectiveness of the lotion preparation in each Example was determined by using a model mouse whose skin is infected with a burn injury by $P.\ acnes$. Specifically, the back of a mouse under anesthesia was shaved with an electric shaver, and a heated weight was pressed thereto, causing a burn injury. After 1 hour, a microbial solution was inoculated to the region beneath the burned site under anesthesia, causing infection. Two hours after infection, the preparation was applied on the burned site of the mouse under anesthesia.

The mouse was euthanized 24 hours after infection, the preparation on the surface of the burned skin site was wiped off, and the burned skin site was collected, cut to smaller pieces and homogenized with a disinfected physiological saline solution. The homogenized solution was diluted as needed and applied on a modified GAM agar flat plate with added rabbit hemolysate. After anaerobic incubation at 37° C. for 7 days, the number of the colonies thereon was counted, and the viable cell count in the skin (LogCFU/skin) was calculated. The results are shown in FIG. 1. As is obvious from FIG. 1, an increase in the content of the compound A leads to an increase in the antimicrobial effect.

Test Example 4

Local Irritation Test

A cumulative irritation test for seven days by using the lotion preparation prepared in Example 3 and four rabbits (Kbl: NZW, female, 17 weeks old) was carried out.

The hair on the back skin of each rabbit was shaved to form an administration site, which was damaged with an injection needle in the checkerboard pattern in the stratum corneum to give abraded skin. The skin was damaged every time before administration. The preparation (0.5 mL) was applied, and then, the abraded skin was covered with a lint cloth, fixed with a bandage and additionally with another bandage together with a urethane plate. The preparation on the administration site was removed on the next day, and the skin condition was observed. The preparation was administered after observation of the skin condition on the second day and later.

In all cases, the skin reaction was evaluated by observing the skin condition about 1 hour after removal of the test substance on each evaluation day, according to the Draize's evaluation criteria shown in Tables 2 and 3.

<Erythema and Crusta>

TABLE 2

| Observation | Score |
|---|---|
| No erythema | 0 |
| Very slight erythema (barely perceptible) | 1 |
| Well defined erythema | 2 |
| Moderate to severe erythema | 3 |
| Severe erythema (beet redness) to slight eschar formation (injuries in depth) | 4 |

<Edema>

TABLE 3

| Observation | Score |
|---|---|
| No edema | 0 |
| Very slight edema (barely perceptible) | 1 |
| Slight edema (edge of area well defined by definite raise) | 2 |
| Moderate edema (area raised approximately 1 mm) | 3 |
| Severe edema (raised more than 1 mm and extending beyond area of exposure) | 4 |

The average score, i.e., the total score (total of the score on erythema and crusta and the score on edema) divided by the number of the application sites, of the abraded skin on each evaluation day was determined, and the change in the average score over time was evaluated.

TABLE 4

| | 1st day | 2nd day | 3rd day | 4th day | 5th day | 6th day | 7th day |
|---|---|---|---|---|---|---|---|
| Example 3 | 1.0 | 1.0 | 1.0 | 0.5 | 0.8 | 0.5 | 0.3 |

Table 4 indicates that the lotion preparation according to the present invention is not irritant.

Example 5 and Comparative Example 1

Desired lotion preparations were prepared in a similar manner to Example 1, according to the composition ratios shown in Table 5. The lotion preparations of Example 5 and Comparative Example 1 were different from each other in that whether the preparation contains ethanol or not.

TABLE 5

| Composition (wt %) | Example 5 | Comparative Example 1 |
|---|---|---|
| Compound A | 1 | 1 |
| Hydroxyethylcellulose | 1 | 1 |
| 1,3-Butylene glycol | 10 | 10 |
| Ethanol | 5 | 0 |
| Potassium hydroxide | 0.43 | 0.43 |
| Sodium bicarbonate | 0.3 | 0.3 |
| Stabilizer | Quantum sufficiat | Quantum sufficiat |
| Purified water | Balance | Balance |
| pH | 10.9 | 10.9 |

Test Example 4

Preservative Effectiveness Test

The test was performed according to the "Preservatives Effectiveness Tests" in the General Information of Japanese Pharmacopoeia, 14th Ed. In short, an indicator strain (*A. niger*) was first incubated on an agar flat plate medium, the colonies were collected aseptically and suspended and dispersed in a disinfected physiological saline solution, and the suspension was filtered through a gauze, to give a filtrate, which was used as an inoculation microbial solution. Then, the inoculation microbial solution was added to each preparation in the same amount, and the mixture was stored at 24° C. for a certain period. The cell counts in the inoculation microbial solution and preparations after 1 week and 2 weeks were determined by an agar pour plate method. The results are shown in FIG. 2.

Figure 2:
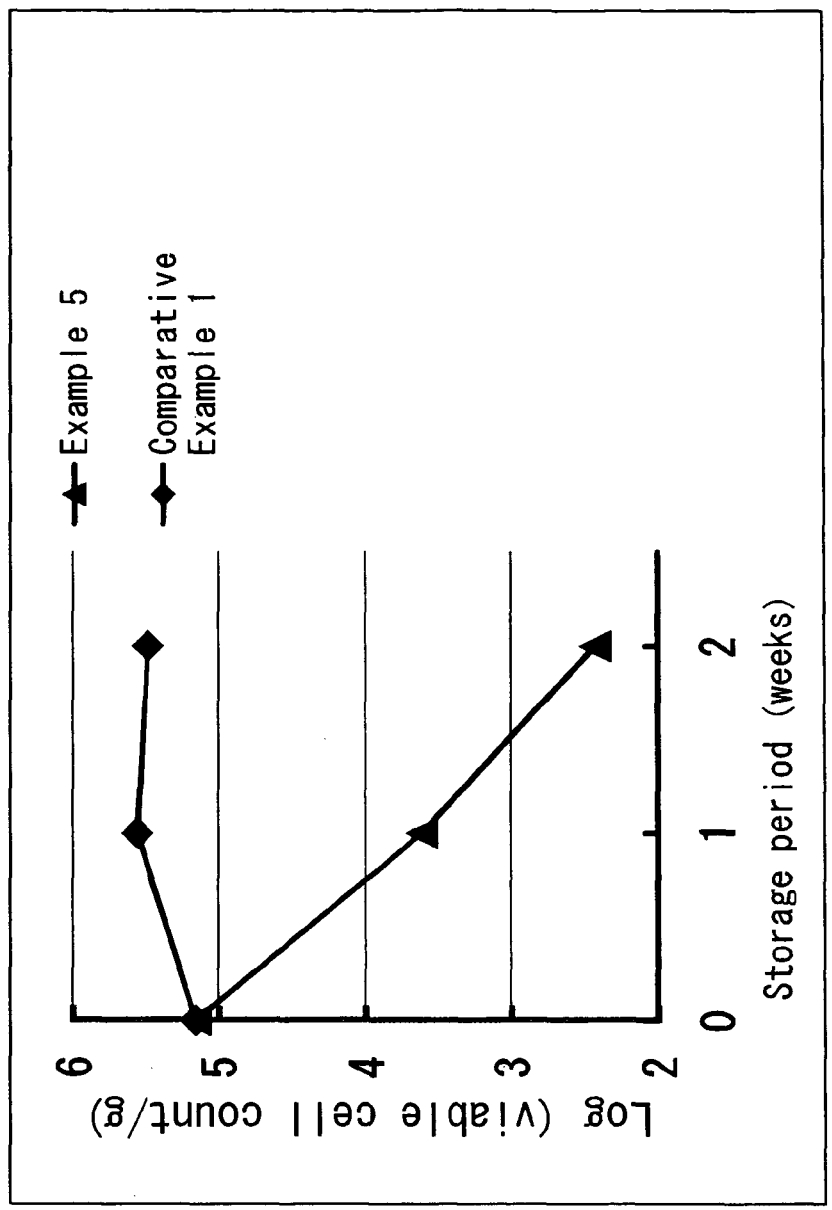
FIG. 2 is a graph showing the results of a preservative effectiveness test.

As is obvious from FIG. 2, the *A. niger* cell count decreased in the lotion preparation (Example 5) containing ethanol and did not decrease in the lotion preparation containing no ethanol (Comparative Example 1). The results indicate that the lotion preparation according to the invention is resistant to contamination by fungi and thus, superior in the storage effect.

The invention claimed is:

1. A lotion preparation, comprising:
   (a) 0.1 to 5 wt % of 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof,
   (b) 1 to 20 wt % of ethanol,
   (c) 0.1 to 5 wt % of a water-soluble cellulose derivative; wherein the cellulose derivative is selected from methylcellulose, hydrophobized hydroxypropylmethylcellulose, hydroxyethylcellulose, or hydroxypropylcellulose, and
   (d) 1 to 30 wt % of 1,3-butylene glycol,
said preparation having a pH of 9 to 12; wherein the preparation does not comprise N-methyl-pyrrolidone.

2. The lotion preparation according to claim 1, wherein the concentration range of the ethanol is 1 to 10 wt %.

3. The lotion preparation according to claim 2, wherein the concentration range of the water-soluble cellulose derivative is 0.7 to 2 wt %.

4. The lotion preparation according to claim 2, wherein the concentration range of the ethanol is 5 to 10 wt %.

5. The lotion preparation according to claim 4, wherein the concentration range of the water-soluble cellulose derivative is 0.7 to 2 wt %.

6. The lotion preparation according to claim 1, wherein the water-soluble cellulose derivative is hydroxyethylcellulose.

7. The lotion preparation according to claim 2, wherein the water-soluble cellulose derivative is hydroxyethylcellulose.

8. The lotion preparation according to claim 3, wherein the water-soluble cellulose derivative is hydroxyethylcellulose.

9. The lotion preparation according to claim 4, wherein the water-soluble cellulose derivative is hydroxyethylcellulose.

10. The lotion preparation according to claim 5, wherein the water-soluble cellulose derivative is hydroxyethylcellulose.

11. A lotion preparation consisting of:
   (a) 0.1 to 5 wt % of 1-cyclopropyl-8-methyl-7-[5-methyl-6-(methylamino)-3-pyridyl]-4-oxo-1,4-dihydro-3-quinolinecarboxylic acid and/or a pharmaceutically acceptable salt thereof,
   (b) 1-20 wt % of ethanol,
   (c) 0.1 to 5 wt % of a water-soluble cellulose derivative; wherein the cellulose derivative is selected from methylcellulose, hydrophobized hydroxypropylmethylcellulose, hydroxyethylcellulose, or hydroxypropylcellulose,
   (d) 1 to 30 wt % of 1,3-butylene glycol, (e) a pH adjustor,
(f) a stabilizer, and
(g) purified water,
said preparation having a pH of 9 to 12.

12. The lotion preparation according to claim 11, wherein the concentration range of the ethanol is 1 to 10 wt %.

13. The lotion preparation according to claim 12, wherein the concentration range of the water-soluble cellulose derivative is 0.7 to 2 wt %.

14. The lotion preparation according to claim 12, wherein the concentration range of the ethanol is 5 to 10 wt %.

15. The lotion preparation according to claim 14, wherein the concentration range of the water-soluble cellulose derivative is 0.7 to 2 wt %.

16. The lotion preparation according to claim 11, wherein the water-soluble cellulose derivative is hydroxyethylcellulose.

17. The lotion preparation according to claim 12, wherein the water-soluble cellulose derivative is hydroxyethylcellulose.

18. The lotion preparation according to claim 13, wherein the water-soluble cellulose derivative is hydroxyethylcellulose.

19. The lotion preparation according to claim 14, wherein the water-soluble cellulose derivative is hydroxyethylcellulose.

20. The lotion preparation according to claim 15, wherein the water-soluble cellulose derivative is hydroxyethylcellulose.

\* \* \* \* \*